(12) United States Patent
Koyakumaru et al.

(10) Patent No.: US 7,560,563 B2
(45) Date of Patent: Jul. 14, 2009

(54) PROCESS FOR PRODUCING 2-SUBSTITUTED PYRIDINE DERIVATIVE

(75) Inventors: Kenichi Koyakumaru, Bizen (JP); Yoshimi Fukunaga, Tokyo (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 517 days.

(21) Appl. No.: 10/522,195

(22) PCT Filed: Jul. 23, 2003

(86) PCT No.: PCT/JP03/09317
§ 371 (c)(1),
(2), (4) Date: Jun. 27, 2005

(87) PCT Pub. No.: WO2004/009551
PCT Pub. Date: Jan. 29, 2004

(65) Prior Publication Data
US 2006/0041142 A1 Feb. 23, 2006

(30) Foreign Application Priority Data
Jul. 23, 2002 (JP) .......................... 2002-214097

(51) Int. Cl.
C07D 401/04 (2006.01)
C07D 405/04 (2006.01)
C07D 413/04 (2006.01)
C07D 417/04 (2006.01)

(52) U.S. Cl. .............. 546/255; 546/268.1; 546/269.1; 546/271.1; 546/271.4; 546/272.1; 546/272.7; 546/275.4; 546/280.4; 546/283.4; 544/224

(58) Field of Classification Search .......... None
See application file for complete search history.

(56) References Cited

U.S. PATENT DOCUMENTS 5,693,611 A 12/1997 Henle et al.
6,169,184 B1 1/2001 Hamprecht et al.

FOREIGN PATENT DOCUMENTS

| JP | 11-269147 | 10/1999 |
|----|-----------|---------|
| JP | 2000-80082 | 3/2000 |
| WO | 98/07700 | 2/1998 |
| WO | 99/65896 | 12/1999 |
| WO | 01/04076 | 1/2001 |

OTHER PUBLICATIONS

Bonnet, Veronique et al. "Syntheses of substituted pyridines, quinolines and diazines via palladium-catalyzed cross-coupling of aryl Grignard reagents", Tetrahedron, vol. 58, No. 22, pp. 4429-4438 2002.
Heirtzler, Fenton R. et al. "Preparation and Characterization of Oligo-(2,2'-bipyridyl)pyrazines", Liebigs Ann./Recueil, pp. 297-301 1997.
Wakabayashi, Shoji et al. "A Cross-Coupling Reaction of Methylsulfinylarene", Bull. Chem. Soc. Jpn., vol. 62, No. 12, pp. 3848-3850 1989.
Jensen, Jacob et al. "Preparation of 2- and 5-Aryl Substituted Thiazoles via Palladium-Catalyzed Negishi Cross-Coupling", Synthesis, No. 1, pp. 128-134 2001.
Zhang, Nan et al. "Palladium-Catalyzed Selective Cross-Coupling between 2-Bromopyridines and Aryl Bromides", J. Org. Chem., vol. 66, No. 4, pp. 1500-1502 2001.
Hargreaves, Stephanie L. et al. "The synthesis of substituted pyridylpyrimidine fungicides using palladium-catalysed cross-coupling reactions", Tetrahedron Letters, vol. 41, No. 10, pp. 1653-1656 2000.
Langli, Geir et al. "Regiochemistry in Stille Couplings of 2,6-Dihalopurines", Tetrahedron, vol. 52, No. 15, pp. 5625-5638 1996.
Schubert, Ulrich S. et al. "Stille-Type Cross-Coupling-An Efficient Way to Various Symmetrically and Unsymmetrically Substituted Methyl-Bipyridines: Toward New ATRP Catalysts", Organic Letters, vol. 2, No. 21, pp. 3373-3376 2000.

*Primary Examiner*—Zinna N Davis
(74) *Attorney, Agent, or Firm*—Oblon, Spivak, McClelland, Maier & Neustadt, P.C.

(57) ABSTRACT

The present invention provides a method of producing a pyridine derivative having a substituent at the 2-position of a heterocyclic structure conveniently and with fine selectivity. The present invention relates to a production method of a pyridine derivative having a substituent at the 2-position of a heterocyclic structure, which is represented by the formula (III), which includes reacting a 2-sulfonylpyridine derivative of the formula (I) with an organometallic compound of the formula (II) and the like, and the like:

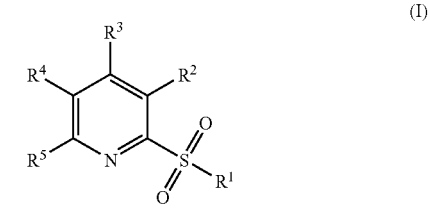

(I)

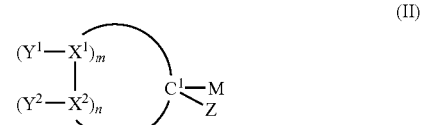

(II)

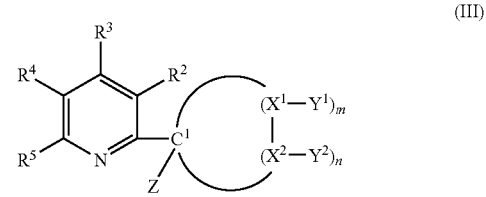

(III)

wherein each symbol is as defined in the Description.

10 Claims, No Drawings

PROCESS FOR PRODUCING 2-SUBSTITUTED PYRIDINE DERIVATIVE

This application claims priority to, and incorporates by reference, International Application NO. PCT/ JP03/09317, filed on Jul. 23, 2003, and Japanese Application 2002-214097, filed on Jul. 23, 2002.

TECHNICAL FIELD

The present invention relates to a production method of a pyridine derivative having a substituent at the 2-position of a heterocyclic structure. The pyridine derivative having a substituent at the 2-position of a heterocyclic structure of the present invention is useful as a synthetic intermediate for an antifungal agent (U.S. Pat. No. 5,693,611).

BACKGROUND ART

Conventionally, as a method of producing a pyridine derivative having a substituent at the 2-position of a heterocyclic structure, (1) a method comprising reacting an organometallic compound having a heterocyclic structure with a 2-halogenated pyridine derivative in the presence of a transition metal catalyst [Synthesis, vol. 1, p. 128 (2001); Journal of Organic Chemistry, vol. 66, No. 4, p. 1500 (2001); WO01/04076 and the like], (2) a method comprising reacting a 2-pyridyl organometallic compound with a halogenated heterocyclic compound in the presence of a transition metal catalyst [Tetrahedron Letters, vol. 41, No. 10, p. 1653 (2000); WO99/65896; Tetrahedron, vol. 52, No. 15, p. 5625 (1996) and the like], (3) a method comprising reacting 2-pyridylsulfoxide with a Grignard reagent having a heterocyclic structure [Liebigs Annalen/Recueil, vol. 2, p. 297 (1997); Bulletin of the Chemical Society of Japan, vol. 62, p. 3848 (1989) and the like] and the like are known.

The above-mentioned methods (1) and (2) require use of a transition metal catalyst, which is expensive and whose waste liquid has a pollution problem, and the reaction does not proceed without the catalyst. In method (3), selectivity of the reaction is low because a bipyridine derivative due to homocoupling reaction is produced as a byproduct.

DISCLOSURE OF THE INVENTION

It is an object of the present invention to provide a method capable of producing a pyridine derivative having a substituent at the 2-position of a heterocyclic structure conveniently with high selectivity.

The present invention relates to

[1] a production method of a pyridine derivative having a substituent at the 2-position of a heterocyclic structure, which is represented by the formula (III')

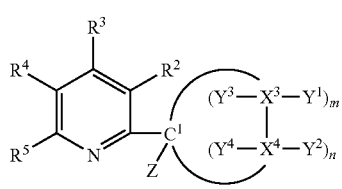

(III')

wherein $R^2$, $R^3$, $R^4$ and $R^5$ are each a hydrogen atom, a halogen atom, an alkyl group optionally having substituent(s), an aryl group optionally having substituent(s), an alkoxyl group optionally having substituent(s), an aryloxy group optionally having substituent(s), an acyloxy group optionally having substituent(s), an alkylthio group optionally having substituent(s), an arylthio group optionally having substituent(s), an acylthio group optionally having substituent(s), a protected amino group optionally having substituent(s), a nitro group, a cyano group, an acyl group optionally having substituent(s), an alkoxycarbonyl group optionally having substituent(s), a carbamoyl group optionally having substituent(s) or a sulfonyl group optionally having substituent(s), or $R^2$ and $R^3$, $R^3$ and $R^4$, and $R^4$ and $R^5$ optionally form, together with a carbon atom bonded thereto, a ring optionally having substituent(s), m and n are each an integer of not less than 1, wherein m+n=3–8, $C^1$ is a carbon atom, Z is a hydrogen atom, an alkyl group optionally having substituent(s) or an aryl group optionally having substituent(s), $X^3$ is a carbon atom, an oxygen atom, a nitrogen atom or a sulfur atom, $X^4$ is a carbon atom, an oxygen atom, a nitrogen atom or a sulfur atom, provided that at least one of $X^3$ and $X^4$ is an oxygen atom, a nitrogen atom or a sulfur atom, when $X^3$ is a nitrogen atom, $Y^3$ bonded to $X^3$ is absent, when $X^3$ is an oxygen atom or a sulfur atom, $Y^1$ and $Y^3$ are absent, when $X^4$ is a nitrogen atom, $Y^4$ bonded to $X^4$ is absent, and when $X^4$ is an oxygen atom or a sulfur atom, $Y^2$ and $Y^4$ are absent, $Y^1$, $Y^2$, $Y^3$ and $Y^4$ are each a hydrogen atom, a halogen atom, an alkyl group optionally having substituent(s), an aryl group optionally having substituent(s), an alkoxyl group optionally having substituent(s), an aryloxy group optionally having substituent(s), an acyloxy group optionally having substituent(s), an alkylthio group optionally having substituent(s), an arylthio group optionally having substituent(s), an acylthio group optionally having substituent(s), a protected amino group optionally having substituent(s), a nitro group, a cyano group, an acyl group optionally having substituent(s), an alkoxycarbonyl group optionally having substituent(s), a carbamoyl group optionally having substituent(s) or a sulfonyl group optionally having substituent(s), or, $Y^1$, $Y^2$ or Z is optionally bonded to $Y^1$ or $Y^2$, which $X^3$ or $X^4$ adjacent to $X^3$, $X^4$ or $C^1$ bonded to $Y^1$, $Y^2$ or Z has, to form a double bond or a ring structure, or $Y^1$ and $Y^3$ optionally represent, in combination, an oxygen atom and are optionally bonded to $X^3$ via a double bond, $Y^2$ and $Y^4$ optionally represent, in combination, an oxygen atom and are optionally bonded to $X^4$ via a double bond [hereinafter to be abbreviated as 2-substituted pyridine derivative (III')], which comprises reacting a 2-sulfonylpyridine derivative represented by the formula (I)

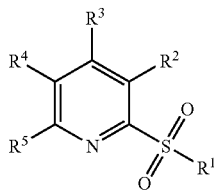

wherein $R^1$ is an alkyl group optionally having substituent(s) or an aryl group optionally having substituent(s), and $R^2$, $R^3$, $R^4$ and $R^5$ are as defined above [hereinafter to be abbreviated as 2-sulfonylpyridine derivative (I)] with an organometallic compound represented by the formula (II')

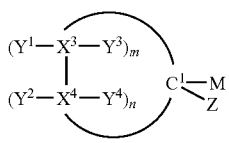

wherein

M is an atom of an element belonging to Group 1, Group 2, Group 12 or Group 13 of the periodic table except a hydrogen atom, and m, n, $C^1$, Z, $X^3$, $X^4$, $Y^1$, $Y^2$, $Y^3$ and $Y^4$ are as defined above [hereinafter to be abbreviated as organometallic compound (II')],

[2] the production method of the above-mentioned [1], wherein $Y^1$ is bonded to $Y^2$, which $X^4$ adjacent $X^3$ bonded to $Y^1$ has, to form a double bond, and at least one of $Y^3$ bonded to said $X^3$ and $Y^4$ bonded to said $X^4$ is an alkyl group optionally having substituent(s),

[3] a production method of a pyridine derivative having a substituent having a heterocyclic structure at the 2-position, which is represented by the formula (III)

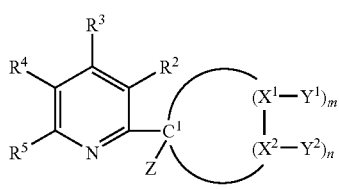

wherein $R^2$, $R^3$, $R^4$ and $R^5$ are as defined above, m and n are each an integer of not less than 1, wherein m+n=3–8, $C^1$ is a carbon atom, Z is a hydrogen atom, an alkyl group optionally having substituent(s) or an aryl group optionally having substituent(s), $X^1$ is a carbon atom, CH, an oxygen atom, a nitrogen atom or a sulfur atom, and $X^2$ is a carbon atom, CH, an oxygen atom, a nitrogen atom or a sulfur atom, provided that at least one of $X^1$ and $X^2$ is an oxygen atom, a nitrogen atom or a sulfur atom, when $X^1$ or $X^2$ is a carbon atom, CH or a nitrogen atom, $Y^1$ and $Y^2$ are each a hydrogen atom, a halogen atom, an alkyl group optionally having substituent(s), an aryl group optionally having substituent(s), an alkoxyl group optionally having substituent(s), an aryloxy group optionally having substituent(s), an acyloxy group optionally having substituent(s), an alkylthio group optionally having substituent(s), an arylthio group optionally having substituent(s), an acylthio group optionally having substituent(s), a protected amino group optionally having substituent(s), a nitro group, a cyano group, an acyl group optionally having substituent(s), an alkoxycarbonyl group optionally having substituent(s), a carbamoyl group optionally having substituent(s) or a sulfonyl group optionally having substituent(s), and $Y^1$, $Y^2$ or Z is optionally bonded to $Y^1$ or $Y^2$, which $X^1$ or $X^2$ adjacent to $X^1$, $X^2$ or $C^1$ bonded to $Y^1$, $Y^2$ or Z has, to form a double bond or a ring structure, or when $X^1$ or $X^2$ is a carbon atom, $Y^1$ or $Y^2$ shows an oxygen atom and is optionally bonded to $X^1$ or $X^2$ via a double bond

[hereinafter to be abbreviated as 2-substituted pyridine derivative (III)], which comprises reacting a 2-sulfonylpyridine derivative (I) with an organometallic compound represented by the formula (II)

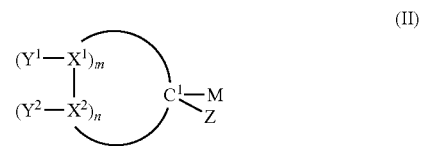

wherein

M is an atom of an element belonging to Group 1, Group 2, Group 12 or Group 13 of the periodic table except a hydrogen atom, and m, n, $C^1$, Z, $X^1$, $X^2$, $Y^1$ and $Y^2$ are as defined above [hereinafter to be abbreviated as organometallic compound (II)],

[4] the production method of the above-mentioned [3], wherein the organometallic compound (II) has an aromatic heterocycle,

[5] the production method of the above-mentioned [4], wherein the aromatic heterocycle is a pyridine ring, a pyrimidine ring, a pyridazine ring, a pyrazine ring, a thiophene ring, a furan ring, a pyrrole ring, an imidazole ring, a pyrazole ring, a thiazole ring, an oxazole ring or an isoxazole ring,

[6] the production method of any of the above-mentioned [3] to [5], wherein, in the formula (II), M is a lithium atom, a sodium atom, a potassium atom, a magnesium atom, a calcium atom, a zinc atom, a boron atom or an aluminum atom, and

[7] the production method of any of the above-mentioned [3] to [5], wherein, in the formula (II), M is a lithium atom or a magnesium atom.

In a preferable embodiment of the present invention, as organometallic compounds (II) and (II'), a compound having an aromatic heterocycle, particularly a pyridine ring, a pyrimidine ring, a pyridazine ring, a pyrazine ring, a thiophene ring, a furan ring, a pyrrole ring, an imidazole ring, a pyrazole ring, a thiazole ring, an oxazole ring or an isoxazole ring is used, and organometallic compounds (II) and (II') of the formulas (II) and (II'), wherein M is a lithium atom, a sodium atom, a potassium atom, a magnesium atom, a calcium atom, a zinc atom, a boron atom or an aluminum atom, particularly organometallic compounds (II) and (II') wherein M is a lithium atom or a magnesium atom, are used.

DETAILED DESCRIPTION OF THE INVENTION

In the present specification, a heterocycle means a ring structure having not less than one atom other than carbon atom in the atom constituting a ring system, and an aromatic heterocycle basically means a 6-membered ring structure having three double bonds in a ring system or a 5-membered ring structure having two double bonds in a ring system.

In the above-mentioned formulas, the alkyl group represented by $R^1$, $R^2$, $R^3$, $R^4$, $R^5$, $Y^1$, $Y^2$, $Y^3$, $Y^4$ or Z, the alkyl group that the alkoxyl group, acyloxy group (alkylcarbonyloxy group), alkylthio group, acylthio group (alkylcarbonylthio group), acyl group (alkylcarbonyl group), alkoxycarbonyl group and sulfonyl group (particularly sulfamoyl group substituted by alkylsulfonyl group, alkoxysulfonyl group, alkyl group and the like) have, each of which is represented by $R^2$, $R^3$, $R^4$, $R^5$, $Y^1$, $Y^2$, $Y^3$ or $Y^4$, and the alkyl group that the protected amino group and carbamoyl group may have as a substituent, each of which is represented by $R^2$, $R^3$, $R^4$, $R^5$, $Y^1$, $Y^2$, $Y^3$ or $Y^4$ may be linear, branched or cyclic and preferably has 1 to 12 carbon atoms. As the alkyl group, for example, methyl group, ethyl group, propyl group, isopropyl group, butyl group, isobutyl group, tert-butyl group, hexyl group, octyl group, dodecyl group, cyclopentyl group, cyclohexyl group and the like can be mentioned.

The ring optionally formed by $R^2$ and $R^3$, $R^3$ and $R^4$ or $R^4$ and $R^5$, together with a carbon atom bonded thereto, is exemplified by, but not particularly limited to, aliphatic carbocycle and the like and preferably has 4 to 10 carbon atoms. As such ring, for example, cyclopentane ring, cyclohexane ring, cyclodecane ring and the like can be mentioned.

The above-mentioned alkyl group and ring optionally have substituent(s) As the substituent, for example, preferably a 5 to 14-membered aryl group having 4 to 15 carbon atoms, which optionally contains a heteroatom such as nitrogen atom, oxygen atom, sulfur atom and the like in the ring structure, such as phenyl group, tolyl group, methoxyphenyl group, chlorophenyl group, bromophenyl group, nitrophenyl group, naphthyl group, anthracenyl group, pyridyl group, furyl group, thienyl group and the like; alkenyl group having 2 or 3 carbon atoms such as vinyl group, 1-methylvinyl group and the like; a halogen atom such as fluorine atom, chlorine atom, bromine atom, iodine atom and the like; a linear, branched or cyclic alkoxyl group having 1 to 12 carbon atoms, such as methoxy group, ethoxy group, propoxy group, isopropoxy group, butoxy group, isobutoxy group, tert-butoxy group, hexyloxy group, octyloxy group, dodecyloxy group, cyclopentyloxy group, cyclohexyloxy group, allyloxy group, benzyloxy group and the like; preferably a 5 to 14-membered aryloxy group having 4 to 15 carbon atoms, which optionally contains a heteroatom such as nitrogen atom, oxygen atom, sulfur atom and the like in the ring structure, such as phenoxy group, chlorophenoxy group, bromophenoxy group, nitrophenoxy group, naphthyloxy group, anthracenyloxy group, pyridyloxy group, furyloxy group, thienyloxy group and the like; a hydroxyl group; a linear, branched or cyclic acyloxy group having 1 to 15 carbon atoms, such as acetyloxy group, propanoyloxy group, butyryloxy group, isobutyryloxy group, valeryloxy group, isovaleryloxy group, pivaloyloxy group, hexanoyloxy group, octanoyloxy group, chloroacetyloxy group, trifluoroacetyloxy group, cyclopentanecarbonyloxy group, cyclohexanecarbonyloxy group, benzoyloxy group, methoxybenzoyloxy group, chlorobenzoyloxy group and the like; a linear, branched or cyclic alkylthio group having 1 to 12 carbon atoms, such as methylthio group, ethylthio group, propylthio group, isopropylthio group, butylthio group, isobutylthio group, tert-butylthio group, hexylthio group, octylthio group, dodecylthio group, cyclopentylthio group, cyclohexylthio group, allylthio group, benzylthio group and the like; preferably a 5 to 14-membered arylthio group having 4 to 15 carbon atoms, which optionally contains a heteroatom such as nitrogen atom, oxygen atom, sulfur atom and the like in the ring structure, such as phenylthio group, tolylthio group, methoxyphenylthio group, chlorophenylthio group, bromophenylthio group, nitrophenylthio group, naphthylthio group, anthracenylthio group, pyridylthio group, furylthio group, thienylthio group and the like; a linear, branched or cyclic acylthio group having 1 to 15 carbon atoms, such as acetylthio group, propanoylthio group, butyrylthio group, isobutyrylthio group, valerylthio group, isovalerylthio group, pivaloylthio group, hexanoylthio group, octanoylthio group, chloroacetylthio group, trifluoroacetyl group, cyclopentanecarbonylthio group, cyclohexanecarbonylthio group, benzoylthio group, naphthoylthio group, anthracenoylthio group, methoxybenzoylthio group, chlorobenzoylthio group and the like; an amino group protected by a protecting group such as acetyl group, benzoyl group, methanesulfonyl group, p-toluenesulfonyl group, tert-butoxycarbonyl group, benzyloxycarbonyl group, allyloxycarbonyl group and the like, wherein the hydrogen atom that the nitrogen atom has is optionally substituted by a linear, branched or cyclic alkyl group having 1 to 12 carbon atoms such as methyl group, ethyl group, propyl group, isopropyl group, butyl group, isobutyl group, tert-butyl group, hexyl group, octyl group, dodecyl group, cyclopentyl group, cyclohexyl group and the like, an alkenyl group having 2 to 3 carbon atoms such as allyl group and the like or an aralkyl group wherein the aryl moiety has 4 to 15 carbon atoms and the alkyl moiety has 1 to 12 carbon atoms, such as benzyl group and the like, and the like; a nitro group; a cyano group; a linear, branched or cyclic acyl group having 1 to 15 carbon atoms, such as acetyl group, propanoyl group, butyryl group, isobutyryl group, valeryl group, isovaleryl group, pivaloyl group, hexanoyl group, octanoyl group, chloroacetyl group, trifluoroacetyl group, cyclopentanecarbonyl group, cyclohexanecarbonyl group, benzoyl group, naphthoyl group, anthracenoyl group, methoxybenzoyl group, chlorobenzoyl group and the like; a linear, branched or cyclic alkoxycarbonyl group having 2 to 13 carbon atoms, such as methoxycarbonyl group, ethoxycarbonyl group, propoxycarbonyl group, isopropoxycarbonyl group, butoxycarbonyl group, isobutoxycarbonyl group, tert-butoxycarbonyl group, hexyloxycarbonyl group, octyloxycarbonyl group, dodecyloxycarbonyl group, cyclopentyloxycarbonyl group, cyclohexyloxycarbonyl group, allyloxycarbonyl group, benzyloxycarbonyl group and the like; a carbamoyl group wherein an optional hydrogen atom that a nitrogen atom has is optionally substituted by a linear, branched or cyclic alkyl group having 1 to 12 carbon atoms, such as methyl group, ethyl group, propyl group, isopropyl group, butyl group, isobutyl group, tert-butyl group, hexyl group, octyl group, dodecyl group, cyclopentyl group, cyclohexyl group and the like, alkenyl group having 2 to 3 carbon atoms, such as allyl group and the like, an aralkyl group wherein the aryl moiety has 4 to 15 carbon atoms and the alkyl moiety has 1 to 12 carbon atoms, such as benzyl group and the like, preferably a 5- to 14-membered aryl group having 4 to 15 carbon atoms, which optionally has a heteroatom such as nitrogen atom, oxygen atom, sulfur atom and the like in the ring structure, and the like, such as phenyl group, tolyl group, methoxyphenyl group, chlorophenyl group, bromophenyl group, nitrophenyl group, naphthyl group, anthracenyl group, pyridyl group, furyl group, thienyl group and the like; a sulfonyl group such as alkylsulfonyl group wherein the alkyl moiety has for example, 1 to 12 carbon atoms (e.g., methanesulfonyl group, ethanesulfonyl group, trifluoromethanesulfonyl group and the like), arylsulfonyl group wherein the aryl moiety has, for example, 4 to 15 carbon atoms (e.g., benzenesulfonyl group, p-toluenesulfonyl group, methoxybenzenesulfonyl group, chlorobenzenesulfonyl group and the like), alkoxysulfonyl group wherein the alkoxyl moiety has, for example, 1 to 12 carbon atoms (e.g., methoxysulfonyl group, ethoxysulfonyl group and the like), sulfamoyl group optionally substituted by, for example, alkyl group having 1 to 12 carbon atoms, aryl group having 4 to 15 carbon atoms and the like (e.g., sulfamoyl group, N,N-dimethylsulfamoyl group, N-phenylsulfamoyl group and the like), and the like; and the like can be mentioned.

As representative examples of the alkoxyl group optionally having substituent(s), methoxy group, ethoxy group, propoxy group, isopropoxy group, butoxy group, isobutoxy group, tert-butoxy group, hexyloxy group, octyloxy group, cyclopentyloxy group, cyclohexyloxy group, allyloxy group, benzyloxy group and the like can be mentioned; as representative examples of the alkylthio group optionally having substituent(s), methylthio group, ethylthio group, propylthio group, isopropylthio group, butylthio group, isobutylthio group, tert-butylthio group, hexylthio group, octylthio group, cyclopentylthio group, cyclohexylthio group, allylthio group, benzylthio group and the like can be mentioned; and as representative examples of the alkoxycarbonyl group optionally having substituent(s), methoxycarbonyl group, ethoxycarbonyl group, propoxycarbonyl group, isopropoxycarbonyl group, butoxycarbonyl group, isobutoxycarbonyl group, tert-butoxycarbonyl group, hexyloxycarbonyl group, octyloxycarbonyl group, cyclopentyloxycarbonyl group, cyclohexyloxycarbonyl group, allyloxycarbonyl group, benzyloxycarbonyl group and the like can be mentioned, each of which is represented by $R^2$, $R^3$, $R^4$, $R^5$, $Y^1$, $Y^2$, $Y^3$ or $Y^4$.

The aryl group represented by $R^1$, $R^2$, $R^3$, $R^4$, $R^5$, $Y^1$, $Y^2$, $Y^3$, $Y^4$ or Z, the aryl group of the aryloxy group, acyloxy group (arylcarbonyloxy group), arylthio group, acylthio group (arylcarbonylthio group), acyl group (arylcarbonyl group) or sulfonyl group (particularly sulfamoyl group substituted by arylsulfonyl group, aryl group and the like), each of which is represented by $R^2$, $R^3$, $R^4$, $R^5$, $Y^1$, $Y^2$, $Y^3$ or $Y^4$, and the aryl group that the amino group or carbamoyl group may have as a substituent, each of which is represented by $R^2$, $R^3$, $R^4$, $R^5$, $Y^1$, $Y^2$, $Y^3$ or $Y^4$, may have a heteroatom such as nitrogen atom, oxygen atom, sulfur atom and the like in the ring structure, and preferably has 4 to 15 carbon atoms. The number of the ring members is preferably 5 to 14. As the aryl group, for example, phenyl group, naphthyl group, anthracenyl group, pyridyl group, furyl group, thienyl group and the like can be mentioned.

The above-mentioned aryl group optionally has substituent(s). As the substituent, for example, a linear, branched or cyclic alkyl group having 1 to 12 carbon atoms, such as methyl group, ethyl group, propyl group, isopropyl group, butyl group, isobutyl group, tert-butyl group, hexyl group, octyl group, dodecyl group, cyclopentyl group, cyclohexyl group and the like; preferably a 5 to 14-membered aryl group having 4 to 15 carbon atoms, which optionally contains a heteroatom such as nitrogen atom, oxygen atom, sulfur atom and the like in the ring structure, such as phenyl group, tolyl group, methoxyphenyl group, chlorophenyl group, bromophenyl group, nitrophenyl group, naphthyl group, anthracenyl group, pyridyl group, furyl group, thienyl group and the like; a halogen atom such as fluorine atom, chlorine atom, bromine atom, iodine atom and the like; a linear, branched or cyclic alkoxyl group having 1 to 12 carbon atoms, such as methoxy group, ethoxy group, propoxy group, isopropoxy group, butoxy group, isobutoxy group, tert-butoxy group, hexyloxy group, octyloxy group, dodecyloxy group, cyclopentyloxy group, cyclohexyloxy group, allyloxy group, benzyloxy group and the like; preferably a 5 to 14-membered aryloxy group having 4 to 15 carbon atoms, which optionally contains a heteroatom such as nitrogen atom, oxygen atom, sulfur atom and the like in the ring structure, such as phenoxy group, chlorophenoxy group, bromophenoxy group, nitrophenoxy group, naphthyloxy group, anthracenyloxy group, pyridyloxy group, furyloxy group, thienyloxy group and the like; a hydroxyl group; a linear, branched or cyclic acyloxy group having 1 to 15 carbon atoms, such as acetyloxy group, propanoyloxy group, butyryloxy group, isobutyryloxy group, valeryloxy group, isovaleryloxy group, pivaloyloxy group, hexanoyloxy group, octanoyloxy group, chloroacetyloxy group, trifluoroacetyl group, cyclopentanecarbonyloxy group, cyclohexanecarbonyloxy group, benzoyloxy group, naphthoyl group, anthracenoyl group, methoxybenzoyloxy group, chlorobenzoyloxy group and the like; a linear, branched or cyclic alkylthio group having 1 to 12 carbon atoms, such as methylthio group, ethylthio group, propylthio group, isopropylthio group, butylthio group, isobutylthio group, tert-butylthio group, hexylthio group, octylthio group, dodecylthio group, cyclopentylthio group, cyclohexylthio group, allylthio group, benzylthio group and the like; preferably a 5 to 14-membered arylthio group having 4 to 15 carbon atoms, which optionally contains a heteroatom such as nitrogen atom, oxygen atom, sulfur atom and the like in the ring structure, such as phenylthio group, tolylthio group, methoxyphenylthio group, chlorophenylthio group, bromophenylthio group, nitrophenylthio group, naphthylthio group, anthracenylthio group, pyridylthio group, furylthio group, thienylthio group and the like; a linear, branched or cyclic acylthio group having 1 to 15 carbon atoms, such as acetylthio group, propanoylthio group, butyrylthio group, isobutyrylthio group, valerylthio group, isovalerylthio group, pivaloylthio group, hexanoylthio group, octanoylthio group, chloroacetylthio group, trifluoroacetylthio group, cyclopentanecarbonylthio group, cyclohexanecarbonylthio group, benzoylthio group, naphthoylthio group, anthracenoylthio group, methoxybenzoylthio group, chlorobenzoylthio group and the like; an amino group protected by a protecting group such as acetyl group, benzoyl group, methanesulfonyl group, p-toluenesulfonyl group, tert-butoxycarbonyl group, benzyloxycarbonyl group, allyloxycarbonyl group and the like, wherein the hydrogen atom that the nitrogen atom has is optionally substituted by a linear, branched or cyclic alkyl group having 1 to 12 carbon atoms such as methyl group, ethyl group, propyl group, isopropyl group, butyl group, isobutyl group, tert-butyl group, hexyl group, octyl group, dodecyl group, cyclopentyl group, cyclohexyl group and the like, an alkenyl group having 2 to 3 carbon atoms such as allyl group and the like or an aralkyl group wherein the aryl moiety has 4 to 15 carbon atoms and the alkyl moiety has 1 to 12 carbon atoms, such as benzyl group and the like, and the like; a nitro group; a cyano group; a linear, branched or cyclic acyl group having 1 to 15 carbon atoms, such as acetyl group, propanoyl group, butyryl group, isobutyryl group, valeryl group, isovaleryl group, pivaloyl group, hexanoyl group, octanoyl group, chloroacetyl group, trifluoroacetyl group, cyclopentanecarbonyl group, cyclohexanecarbonyl group, benzoyl group, naphthoyl group, anthracenoyl group, methoxybenzoyl group, chlorobenzoyl group and the like; a linear, branched or cyclic alkoxycarbonyl group having 2 to 13 carbon atoms, such as methoxycarbonyl group, ethoxycarbonyl group, propoxycarbonyl group, isopropoxycarbonyl group, butoxycarbonyl group, isobutoxycarbonyl group, tert-butoxycarbonyl group, hexyloxycarbonyl group, octyloxycarbonyl group, dodecyloxycarbonyl group, cyclopentyloxycarbonyl group, cyclohexyloxycarbonyl group, allyloxycarbonyl group, benzyloxycarbonyl group and the like; a carbamoyl group wherein an optional hydrogen atom that a nitrogen atom has is optionally substituted by a linear, branched or cyclic alkyl group having 1 to 12 carbon atoms, such as methyl group, ethyl group, propyl group, isopropyl group, butyl group, isobutyl group, tert-butyl group, hexyl group, octyl group, dodecyl group, cyclopentyl group, cyclohexyl group and the like, alkenyl group having 2 to 3 carbon atoms, such as allyl group and the like, an aralkyl group wherein the aryl moiety has 4 to 15 carbon atoms and the alkyl moiety has 1 to 12 carbon atoms, such as benzyl group and the like, preferably a 5- to 14-membered aryl group having 4 to 15 carbon atoms, which optionally has a heteroatom such as nitrogen atom, oxygen atom, sulfur atom and the like in the ring structure, such as phenyl group, tolyl group, methoxyphenyl group, chlorophenyl group, bromophenyl group, nitrophenyl group, naphthyl group, anthracenyl group, pyridyl group, furyl group, thienyl group and the like, and the like; a sulfonyl group such as alkylsulfonyl group wherein the alkyl moiety has for example, 1 to 12 carbon atoms (e.g., methanesulfonyl group, ethanesulfonyl group, trifluoromethanesulfonyl group and the like), arylsulfonyl group wherein the aryl moiety has, for example, 4 to 15 carbon atoms (e.g., benzenesulfonyl group, p-toluenesulfonyl group, methoxybenzenesulfonyl group, chlorobenzenesulfonyl group and the like), alkoxysulfonyl group wherein the alkoxyl moiety has, for example, 1 to 12 carbon atoms (e.g., methoxysulfonyl group, ethoxysulfonyl group and the like), sulfamoyl group optionally substituted by, for example, alkyl group having 1 to 12 carbon atoms, aryl group having 4 to 15 carbon atoms and the like (e.g., sulfamoyl group, N,N-dimethylsulfamoyl group, N-phenylsulfamoyl group and the like), and the like; and the like can be mentioned.

As representative examples of aryloxy group, phenoxy group, chlorophenoxy group, bromophenoxy group, nitrophenoxy group, naphthyloxy group, pyridyloxy group, furyloxy group, thienyloxy group and the like can be mentioned; as representative examples of arylthio group, phenylthio group, chlorophenylthio group, bromophenylthio group, nitrophenylthio group, naphthylthio group, pyridylthio group, furylthio group, thienylthio group and the like can be mentioned; and as a halogen atom, for example, fluorine atom, chlorine atom, bromine atom, iodine atom can be mentioned, each of which is represented by $R^2$, $R^3$, $R^4$, $R^5$, $Y^1$, $Y^2$, $Y^3$ or $Y^4$.

In the protected amino group optionally having substituent(s), which is represented by $R^2$, $R^3$, $R^4$, $R^5$, $Y^1$, $Y^2$, $Y^3$ or $Y^4$, as the protecting group, for example, acetyl group, benzoyl group, methanesulfonyl group, p-toluenesulfonyl group, tert-butoxycarbonyl group, benzyloxycarbonyl group, allyloxycarbonyl group and the like can be mentioned, and as the substituent of the hydrogen atom that the nitrogen atom has, alkyl group and aryl group mentioned above can be used. As this substituent, alkenyl group, aralkyl group and the like are also used. As representative examples of the amino group, N-methyl-N-tert-butoxycarbonylamino group, N-ethyl-N-benzyloxycarbonylamino group, N-benzyl-N-acetylamino group, N-allyl-N-benzoylamino group, N-phenyl-N-methanesulfonylamino group and the like can be mentioned.

In the carbamoyl group optionally having substituent(s), which is represented by $R^2$, $R^3$, $R^4$, $R^5$, $Y^1$, $Y^2$, $Y^3$ or $Y^4$, the substituent of the optional hydrogen atom that the nitrogen atom has may be any of the alkyl group and aryl group defined above, or may be alkenyl group, aralkyl group and the like. As representative examples of the carbamoyl group, N,N-dimethylcarbamoyl group, N,N-diisopropylcarbamoyl group, N-methyl-N-phenylcarbamoyl group, N-benzyl-N-phenylcarbamoyl group, N-allyl-N-naphthylcarbamoyl group, N,N-diphenylcarbamoyl group and the like can be mentioned.

The acyl group represented by $R^2$, $R^3$, $R^4$, $R^5$, $Y^1$, $Y^2$, $Y^3$ or $Y^4$ may be any of the alkylcarbonyl group and arylcarbonyl group defined above. As representative examples of the acyl group, acetyl group, propanoyl group, butyryl group, isobutyryl group, valeryl group, isovaleryl group, pivaloyl group, hexanoyl group, octanoyl group, dodecanoyl group, chloroacetyl group, trifluoroacetyl group, cyclopentanecarbonyl group, cyclohexanecarbonyl group, benzoyl group, naphthoyl group, anthracenoyl group, methoxybenzoyl group, chlorobenzoyl group and the like can be mentioned.

The acyloxy group represented by $R^2$, $R^3$, $R^4$, $R^5$, $Y^1$, $Y^2$, $Y^3$ or $Y^4$ may be either the alkylcarbonyloxy group or arylcarbonyloxy group defined above. As representative examples of the acyloxy group, acetyloxy group, propanoyloxy group, butyryloxy group, isobutyryloxy group, valeryloxy group, isovaleryloxy group, pivaloyloxy group, hexanoyloxy group, octanoyloxy group, dodecanoyloxy group, chloroacetyloxy group, trifluoroacetyloxy group, cyclopentanecarbonyloxy group, cyclohexanecarbonyloxy group, benzoyloxyoxy group, naphthoyloxy group, anthracenyloxy group, methoxybenzoyloxy group, chlorobenzoyloxy group and the like can be mentioned.

The acylthio group represented by $R^2$, $R^3$, $R^4$, $R^5$, $Y^1$, $Y^2$, $Y^3$ or $Y^4$ may be either the alkylcarbonylthio group or arylcarbonylthio group defined above. As representative examples of the acylthio group, acetylthio group, propanoylthio group, butyrylthio group, isobutyrylthio group, valerylthio group, isovalerylthio group, pivaloylthio group, hexanoylthio group, octanoylthio group, dodecanoylthio group, chloroacetylthio group, trifluoroacetylthio group, cyclopentanecarbonylthio group, cyclohexanecarbonylthio group, benzoylthio group, naphthoylthio group, anthracenoylthio group, methoxybenzoylthio group, chlorobenzoylthio group and the like can be mentioned.

As the sulfonyl group represented by $R^2$, $R^3$, $R^4$, $R^5$, $Y^1$, $Y^2$, $Y^3$ or $Y^4$, for example, sulfamoyl group optionally substituted by alkylsulfonyl group, arylsulfonyl group, alkoxysulfonyl group, alkyl group, aryl group and the like, and the like can be mentioned. For example, an alkylsulfonyl group wherein the alkyl moiety has, for example, 1 to 12 carbon atoms, such as methanesulfonyl group, ethanesulfonyl group, trifluoromethanesulfonyl group and the like; an arylsulfonyl group wherein the aryl moiety has, for example, 4 to 15 carbon atoms, such as benzenesulfonyl group, p-toluenesulfonyl group, methoxybenzenesulfonyl group, chlorobenzenesulfonyl group and the like; an alkoxysulfonyl group wherein the alkoxyl moiety has, for example, 1 to 12 carbon atoms, such as methoxysulfonyl group, ethoxysulfonyl group and the like; a sulfamoyl group optionally substituted by, for example, alkyl group having 1 to 12 carbon atoms, aryl group having 4 to 15 carbon atoms and the like (e.g., sulfamoyl group, N,N-dimethylsulfamoyl group, N-phenylsulfamoyl group and the like); and the like can be mentioned.

In the above-mentioned formulas (II') and (III'), $X^3$ and $X^4$ are each a carbon atom, an oxygen atom, a nitrogen atom or a sulfur atom, provided that at least one of $X^3$ and $X^4$ is an oxygen atom, a nitrogen atom or a sulfur atom, when $X^3$ is a nitrogen atom, $Y^3$ to be bonded to $X^3$ is absent, when $X^3$ is an oxygen atom or a sulfur atom, $Y^1$ and $Y^3$ are absent, when $X^4$ is a nitrogen atom, $Y^4$ to be bonded to $X^4$ is absent, and when $X^4$ is an oxygen atom or a sulfur atom, $Y^2$ and $Y^4$ are absent.

In the above-mentioned formulas (II) and (III), $X^1$ and $X^2$ are each a carbon atom, CH, an oxygen atom, a nitrogen atom or a sulfur atom, provided that at least one of $X^1$ and $X^2$ is an oxygen atom, a nitrogen atom or a sulfur atom, when $X^1$ is an oxygen atom or a sulfur atom, $Y^1$ to be bonded to $X^1$ is absent, and when $X^2$ is an oxygen atom or a sulfur atom, $Y^2$ to be bonded to $X^2$ is absent.

In the above-mentioned formulas (II), (II'), (III) and (III'), when m is not less than 2, two or more $X^1$ may be the same or different, two or more $Y^1$ may be the same or different, two or more $X^3$ may be the same or different, and two or more $Y^3$ may be the same or different. Similarly, when n is not less than 2, two or more $X^2$, $Y^2$, $X^4$ and $Y^4$ may be independently the same or different.

Thus, organometallic compounds (II) and (II') have a heterocycle. As the heterocycle, for example, aliphatic heterocycles such as azetidine ring, pyrrolidine ring, piperidine ring, tetrahydrofuran ring, tetrahydropyran ring, tetrahydrothiophene ring and the like, and the like can be mentioned. The carbon atom and nitrogen atom constituting these heterocycles can have the above-mentioned atom or substituent represented by $Y^1$, $Y^2$ or Z. In organometallic compound (II'), the carbon atom can further have an atom or substituent represented by $Y^3$ or $Y^4$. The oxygen atom and sulfur atom constituting the heterocycle do not have the above-mentioned atom or substituent represented by $Y^1$, $Y^2$, $Y^3$ or $Y^4$.

In the above-mentioned formula (II), $Y^1$, $Y^2$ or Z is optionally bonded to $Y^1$ or $Y^2$, which $X^1$ or $X^2$ adjacent to $X^1$, $X^2$ or $C^1$ bonded to $Y^1$, $Y^2$ or Z has, to form a double bond. In the above-mentioned formula (II'), $Y^1$, $Y^2$ or Z is optionally bonded to Y1 or $Y^2$, which $X^3$ or $X^4$ adjacent to $X^3$, $X^4$ or $C^1$ bonded to $Y^1$, $Y^2$ or Z has, to form a double bond. As a heterocycle having such a double bond, for example, aromatic heterocycles such as pyridine ring, pyrimidine ring, pyridazine ring, pyrazine ring, 1,2,4-triazine ring, 1,3,5-triazine ring, thiophene ring, furan ring, pyrrole ring, imidazole ring, pyrazole ring, thiazole ring, oxazole ring, isoxazole ring, 1,2,3-triazole ring, 1,2,4-triazole ring, tetrazole ring and the like; aliphatic heterocycles such as 1,2,3,6-tetrahydropyridine, 1,2,3,4-tetrahydropyridine, 2,3-dihydrofuran, 2,5-dihydrofuran, 3,4-dihydro-2H-pyran, 5,6-dihydro-2H-pyran, 2,5-dihydropyrrole, imidazoline, thiazoline, oxazoline and the like; and the like can be mentioned.

In the above-mentioned formula (II), when $X^1$ or $X^2$ is a carbon atom, $Y^1$ and $Y^2$ may be each an oxygen atom, and may be bonded to $X^1$ or $X^2$ via a double bond. In the above-mentioned formula (II'), $Y^1$ and $Y^3$ optionally represent, in combination, an oxygen atom and are optionally bonded to $X^3$ via a double bond, and $Y^2$ and $Y^4$ optionally represent, in combination, an oxygen atom and are optionally bonded to $X^4$ via a double bond. As a heterocycle having such a double bond, for example, lactones such as γ-butyrolactone, 2,5-dihydrofuran-2-one, tetrahydropyran-2-one, 5,6-dihydro-2H-pyran-2-one, 2(5H)-furanone and the like; lactams such as 2-azetidinone, 2-pyrrolidinone, 2-piperidinone, 1,2,5,6-tetrahydropyridine-2-one, 2,5-dihydropyrrol-2-one and the like; cyclic acid anhydrides such as succinic anhydride, maleic anhydride, glutaric anhydride and the like; imides such as succinimide, maleimide, glutarimide and the like; 2-imidazolidinone, 2-oxazolidinone, 2-thiazolidinone, 3,4,5,6-tetrahydro-2(1H)-pyrimidinone, hydantoin; and the like can be mentioned.

In the above-mentioned formula (II), $Y^1$, $Y^2$ or Z is optionally bonded to $Y^1$ or $Y^2$, which $X^1$ or $X^2$ adjacent to $X^1$, $X^2$ or $C^1$ bonded to $Y^1$, $Y^2$ or Z has, to form a ring structure. In the above-mentioned formula (II'), moreover, $Y^1$, $Y^2$ or Z is optionally bonded to $Y^1$ or $Y^2$, which $X^3$ or $X^4$ adjacent to $X^3$, $X^4$ or $C^1$ bonded to $Y^1$, $Y^2$ or Z has, to form a ring structure. As such ring structure, preferably a 4- to 14-membered aromatic or aliphatic carbocycle or heterocycle optionally substituted by one or more oxo groups and the like, which may have a heteroatom such as nitrogen atom, oxygen atom, sulfur atom and the like in the ring structure, and the like can be mentioned. As such ring structure, for example, aromatic carbocycles such as benzene, naphthalene, anthracene and the like; aliphatic carbocycles such as cyclopentane, cyclohexane, cycloheptane and the like; aromatic heterocycles such as pyridine, pyrimidine, pyridazine, pyrazine, 1,2,4-triazine, 1,3,5-triazine, thiophene, furan, pyrrole, imidazole, pyrazole, thiazole, oxazole, isoxazole, 1,2,3-triazole, 1,2,4-triazole, tetrazole and the like; aliphatic heterocycles such as azetidine, pyrrolidine, piperidine, tetrahydrofuran, tetrahydropyran, tetrahydrothiophene and the like; lactone rings such as γ-butyrolactone, 2,5-dihydrofuran-2-one, tetrahydropyran-2-one, 5,6-dihydro-2H-pyran-2-one, 2(5H)-furanone and the like; lactam rings such as 2-azetidinone, 2-pyrrolidinone, 2-piperidinone, 1,2,5,6-tetrahydropyridine-2-one, 2,5-dihydropyrrol-2-one and the like; acid anhydride rings such as succinic anhydride, maleic anhydride, glutaric anhydride and the like; imide rings such as succinimide, maleimide, glutarimide and the like; a ring such as 2-imidazolidinone, 2-oxazolidinone, 2-thiazolidinone, 3,4,5,6-tetrahydro-2(1H)-pyrimidinone, hydantoin and the like; and the like can be mentioned.

As organometallic compounds (II) and (II'), a compound having an aromatic heterocycle, particularly a compound having pyridine ring, pyrimidine ring, pyridazine ring, pyrazine ring, thiophene ring, furan ring, pyrrole ring, imidazole ring, pyrazole ring, thiazole ring, oxazole ring or isoxazole ring is preferable.

As organometallic compounds (II) and (II'), organometallic compounds of the above-mentioned formulas (II) and (II'), wherein M is lithium atom, sodium atom, potassium atom, magnesium atom, calcium atom, zinc atom, boron atom or aluminum atom, are preferable, and an organometallic compound wherein M is lithium atom or magnesium atom is more preferable.

The reaction is preferably carried out in the presence of a solvent. The solvent is not particularly limited as long as it does not adversely affect the reaction. For example, aliphatic hydrocarbons such as hexane, heptane, octane and the like; aromatic hydrocarbons such as benzene, toluene, xylene, ethylbenzene, mesitylene and the like; ethers such as tetrahydrofuran, diethyl ether, diisopropyl ether, tert-butylmethyl ether, 1,2-dimethoxyethane, 1,4-dioxane, diglyme and the like; and the like can be mentioned. Of these, ethers such as tetrahydrofuran, diethyl ether, diisopropyl ether, tert-butylmethyl ether, 1,2-dimethoxyethane, 1,4-dioxane, diglyme and the like are preferable, and tetrahydrofuran is particularly preferable. The solvent may be used alone or in a combination of two or more kinds thereof. The amount of the solvent to be used is within the range of generally 0.5- to 100-fold by weight, preferably 1- to 20-fold by weight, relative to 2-sulfonylpyridine derivative (I).

The amount of the organometallic compounds (II) and (II') to be used is preferably within the range of 0.1 to 10 equivalents, more preferably 0.5 to 3 equivalents, relative to 2-sulfonylpyridine derivative (I).

The reaction temperature is preferably within the range of −100° C. to 100° C., more preferably −80° C. to 50° C. The reaction time is within the range of generally 0.1-40 hr, preferably 0.5-20 hr.

As the reaction operation, 2-sulfonylpyridine derivative (I) is added to a given amount of organometallic compound (II) or (II') prepared in advance; otherwise organometallic compound (II) or (II') is added to a solution of 2-sulfonylpyridine derivative (I). During addition, organometallic compound (II), (II') or 2-sulfonylpyridine derivative (I) may be diluted with the above-mentioned reaction solvent. While the concentration after dilution is not particularly limited, organometallic compounds (II), (II') or 2-sulfonylpyridine derivative (I) preferably have a concentration within the range of 1-80 wt %, more preferably 5-50 wt %. While the rate of addition is not particularly limited, it is preferably such speed that enables control of the temperature to a level to obtain a good reaction result.

The 2-substituted pyridine derivatives (III) and (III') produced by the present invention can be isolated or purified by methods generally used for the isolation or purification of organic compounds. For example, water is added to a reaction mixture, then the mixture is extracted by adding an organic solvent such as hexane, toluene, xylene, tetrahydrofuran, diisopropyl ether, tert-butylmethyl ether, ethyl acetate, butyl acetate and the like, the extract is concentrated and the obtained crude product is purified as necessary by distillation, recrystallization, chromatography and the like.

The 2-sulfonylpyridine derivative (I), which is a starting material, can be easily produced from, for example, $\alpha,\beta$-unsaturated carbonyl compounds and sulfonylcyanides (see JP-A-11-269147). In addition, organometallic compound (II) can be produced by, for example, the reaction between the corresponding halide and an organic lithium reagent [see Organic Letters, vol. 2, No. 21, p. 3373 (2000)].

EXAMPLES

The present invention is explained in detail by referring to Examples, which are not to be construed as limitative.

Example 1

Synthesis of 2,4'-bipyridine

Tetrahydrofuran (10 ml) was charged in a nitrogen-substituted flask having an inner volume of 50 ml, cooled to −78° C., and a solution (1.6 M, 10.3 ml, 16.4 mmol) of n-butyllithium in hexane was added. To this solution was added dropwise over 10 min a solution obtained by dissolving 4-bromopyridine (2.59 g, 16.4 mmol) in tetrahydrofuran (3 ml). The reaction mixture was stirred for 1 hr and a solution obtained by dissolving 2-benzenesulfonylpyridine (3.00 g, 13.7 mmol) in tetrahydrofuran (5 ml) was added dropwise over 10 min. The reaction mixture was stirred for 3 hr, and isopropanol (1 ml) was added at the same temperature to stop the reaction.

The obtained reaction mixture was added to water, and the mixture was extracted with ethyl acetate (15 ml×2). The extract was concentrated and purified by silica gel chromatography to give the title compound having the following analytical data (1.75 g, yield 81% based on 2-benzenesulfonylpyridine) as a white solid.

$^1$H-NMR spectrum (CDCl$_3$) δ: 7.33-7.37 (m, 1H), 7.80-7.91 (m, 4H), 8.72-8.76 (m, 3H)

Example 2

Synthesis of 4-methyl-2-(2'-pyridyl)pyridine

Tetrahydrofuran (10 ml) and isopropylmagnesium chloride (2.0 M, 7.7 ml, 15.5 mmol) were charged in a nitrogen-substituted flask having an inner volume of 50 ml and then a solution obtained by dissolving 2-bromopyridine (2.45 g, 15.5 mmol) in tetrahydrofuran (3 ml) was added dropwise over 10 min. The reaction mixture was stirred for 1 hr, and a solution obtained by dissolving 4-methyl-2-benzenesulfonylpyridine (3.00 g, 12.9 mmol) in tetrahydrofuran (5 ml) was added dropwise over 10 min. The reaction mixture was stirred at room temperature for 5 hr, and isopropanol (1 ml) was added to stop the reaction.

The obtained reaction mixture was added to water, and the mixture was extracted with ethyl acetate (15 ml×2). The extract was concentrated and purified by silica gel chromatography to give the title compound (1.51 g, yield 89% based on 4-methyl-2-benzenesulfonylpyridine) having the following analytical data as a white solid.

$^1$H-NMR spectrum (CDCl$_3$) δ: 2.36 (s, 3H), 7.06 (d, 1H, J=5.0 Hz), 7.20-7.25 (m, 1H), 7.69-7.74 (m, 1H), 8.16 (s, 1H), 8.32 (d, 1H, J=8.0 Hz), 8.46 (d, 1H, J=4.6 Hz), 8.57-8.63 (m, 1H)

Example 3

Synthesis of 2,3'-bipyridine

Tetrahydrofuran (10 ml) and isopropylmagnesium chloride (2.0 M, 8.2 ml, 16.4 mmol) were charged in a nitrogen-substituted flask having an inner volume of 50 ml and then a solution obtained by dissolving 3-bromopyridine (2.59 g, 16.4 mmol) in tetrahydrofuran (3 ml) was added dropwise over 10 min. The reaction mixture was stirred for 1 hr, and a solution obtained by dissolving 2-benzenesulfonylpyridine (3.00 g, 13.7 mmol) in tetrahydrofuran (5 ml) was added dropwise over 10 min. The reaction mixture was stirred at room temperature for 5 hr, and isopropanol (1 ml) was added to stop the reaction.

The obtained reaction mixture was added to water, and the mixture was extracted with ethyl acetate (15 ml×2). The extract was concentrated and purified by silica gel chromatography to give the title compound (1.65 g, yield 91% based on 2-benzenesulfonylpyridine) having the following analytical data as a colorless oil.

$^1$H-NMR spectrum (CDCl$_3$) δ: 7.23-7.58 (m, 2H), 7.70-7.91 (m, 2H), 8.33-8.39 (m, 1H), 8.62-8.88 (m, 2H), 9.20 (d, 1H, J=3.0 Hz)

Example 4

Synthesis of 6-chloro-2-(2'-thienyl)pyridine

Tetrahydrofuran (15 ml) and magnesium (480 mg, 19.7 mmol) were charged in a nitrogen-substituted flask having an inner volume of 50 ml, and then a solution obtained by dissolving 2-bromothiophene (2.67 g, 16.4 mmol) in tetrahydrofuran (3 ml) was added dropwise over 10 min. The reaction mixture was stirred for 1 hr, and a solution obtained by dissolving 6-chloro-2-benzenesulfonylpyridine (3.00 g, 13.7 mmol) in tetrahydrofuran (5 ml) was added dropwise over 10 min. The reaction mixture was stirred at room temperature for 5 hr, and isopropanol (1 ml) was added to stop the reaction.

The obtained reaction mixture was added to water, and the mixture was extracted with ethyl acetate (15 ml×2). The extract was concentrated and purified by silica gel chromatography to give the title compound (1.72 g, yield 78% based on 6-chloro-2-benzenesulfonylpyridine) having the following analytical data as a colorless oil.

$^1$H-NMR spectrum (CDCl$_3$) δ: 7.12-7.17 (m, 2H), 7.47-7.55 (m, 2H), 7.62-7.74 (m, 2H)

Example 5

Synthesis of 2-(3'-thienyl)pyridine

Tetrahydrofuran (10 ml) was charged in a nitrogen-substituted flask having an inner volume of 50 ml, cooled to −78° C., and a solution (1.6 M, 10.3 ml, 16.4 mmol) of n-butyllithium in hexane was added. To this solution was added dropwise over 10 min a solution obtained by dissolving 3-bromothiophene (2.67 g, 16.4 mmol) in tetrahydrofuran (3 ml ). The reaction mixture was stirred for 30 min, and a solution obtained by dissolving 2-benzenesulfonylpyridine (3.00 g, 13.7 mmol) in tetrahydrofuran (5 ml) was added dropwise over 10 min. The reaction mixture was stirred for 3 hr, and isopropanol (1 ml) was added at the same temperature to stop the reaction.

The obtained reaction mixture was added to water, and the mixture was extracted with ethyl acetate (15 ml×2). The extract was concentrated and purified by silica gel chromatography to give the title compound (1.83 g, yield 83% based on 2-benzenesulfonylpyridine) having the following analytical data as a colorless oil.

$^1$H-NMR spectrum (CDCl$_3$) δ: 7.14-7.19 (m, 1H), 7.39 (dd, 1H, J=3.2 Hz, 5.0 Hz), 7.60-7.73 (m, 3H), 7.90 (dd, 1H, J=0.8 Hz, 3.2 Hz), 8.60-8.63 (m, 1H)

Example 6

Synthesis of 2-(2'-furyl)pyridine

Tetrahydrofuran (10 ml) was charged in a nitrogen-substituted flask having an inner volume of 50 ml, cooled to −78° C., and a solution (1.6 M, 10.3 ml, 16.4 mmol) of n-butyllithium in hexane was added. To this solution was added dropwise over 10 min a solution obtained by dissolving 2-bromofuran (2.38 g, 16.4 mmol) in tetrahydrofuran (3 ml ). The reaction mixture was stirred for 30 min, and a solution obtained by dissolving 2-benzenesulfonylpyridine (3.00 g, 13.7 mmol) in tetrahydrofuran (5 ml) was added dropwise over 10 min. The reaction mixture was stirred for 3 hr, and isopropanol (1 ml) was added at the same temperature to stop the reaction.

The obtained reaction mixture was added to water, and the mixture was extracted with ethyl acetate (15 ml×2). The extract was concentrated and purified by silica gel chromatography to give the title compound (1.45 g, yield 73% based on 2-benzenesulfonylpyridine) having the following analytical data as a colorless oil.

$^1$H-NMR spectrum (CDCl$_3$) d: 6.50-6.63 (m, 1H), 6.84-7.23 (m, 2H), 7.50-7.83 (m, 3H), 8.58-8.73 (m, 1H)

Example 7

Synthesis of 2-(1'-benzyloxy-5'-pyrazolyl)pyridine

Tetrahydrofuran (10 ml) was charged in a nitrogen-substituted flask having an inner volume of 50 ml, cooled to −78° C., and a solution (1.6 M, 10.3 ml, 16.4 mmol) of n-butyllithium in hexane was added. To this solution was added dropwise over 10 min a solution obtained by dissolving 1-benzyloxypyrazole (2.86 g, 16.4 mmol) in tetrahydrofuran (3 ml ). The reaction mixture was stirred for 30 min, and a solution obtained by dissolving 2-benzenesulfonylpyridine (3.00 g, 13.7 mmol) in tetrahydrofuran (5 ml) was added dropwise over 10 min. The reaction mixture was stirred for 3 hr, and isopropanol (1 ml) was added at the same temperature to stop the reaction.

The obtained reaction mixture was added to water, and the mixture was extracted with ethyl acetate (15 ml×2). The extract was concentrated and purified by silica gel chromatography to give the title compound (2.90 g, yield 84% based on 2-benzenesulfonylpyridine) having the following analytical data as a white solid.

$^1$H-NMR spectrum (CDCl$_3$) δ: 5.30 (s, 2H), 6.68 (d, 1H, J=2.4 Hz)), 7.19-7.18 (m, 6H), 7.37 (d, 1H, J=2.4 Hz), 7.64-7.77 (m, 2H), 8.62 (dd, 1H, J=1.8 Hz, 4.8 Hz)

Example 8

Synthesis of 2-(4'-methyl-2'-oxazolyl)pyridine

Tetrahydrofuran (10 ml) was charged in a nitrogen-substituted flask having an inner volume of 50 ml, cooled to −78° C., and a solution (1.6 M, 10.3 ml, 16.4 mmol) of n-butyllithium in hexane was added. To this solution was added dropwise over 10 min a solution obtained by dissolving 4-methyloxazole (1.36 g, 16.4 mmol) in tetrahydrofuran (3 ml). The reaction mixture was stirred for 30 min, and a solution obtained by dissolving 2-benzenesulfonylpyridine (3.00 g, 13.7 mmol) in tetrahydrofuran (5 ml) was added dropwise over 10 min. The reaction mixture was stirred for 3 hr, and isopropanol (1 ml) was added at the same temperature to stop the reaction.

The obtained reaction mixture was added to water, and the mixture was extracted with ethyl acetate (15 ml×2). The extract was concentrated and purified by silica gel chromatography to give the title compound having the following analytical data (1.51 g, yield 69% based on 2-benzenesulfonylpyridine) as a white solid.

$^1$H-NMR spectrum (CDCl$_3$) δ: 2.29 (d, 3H, J=1.6 Hz), 7.39-7.45 (m, 1H), 7.62 (q, 1H, J=1.6 Hz), 7.86-7.92 (m, 1H), 8.17-8.23 (m, 1H), 8.82-8.86 (m, 1H)

Example 9

Synthesis of 2-(2'-thiazolyl)pyridine

Tetrahydrofuran (10 ml) was charged in a nitrogen-substituted flask having an inner volume of 50 ml, cooled to −78° C., and a solution (1.6 M, 10.3 ml, 16.4 mmol) of n-butyllithium in hexane was added. To this solution was added dropwise over 10 min a solution obtained by dissolving thiazole (1.40 g, 16.4 mmol) in tetrahydrofuran (3 ml). The reaction mixture was stirred for 30 min, and a solution obtained by dissolving 2-benzenesulfonylpyridine (3.00 g, 13.7 mmol) in tetrahydrofuran (5 ml) was added dropwise over 10 min. The reaction mixture was stirred for 3 hr, and isopropanol (1 ml) was added at the same temperature to stop the reaction.

The obtained reaction mixture was added to water, and the mixture was extracted with ethyl acetate (15 ml×2). The extract was concentrated and purified by silica gel chromatography to give the title compound having the following analytical data (1.22 g, yield 55% based on 2-benzenesulfonylpyridine) as a pale-yellow solid.

$^1$H-NMR spectrum (CDCl$_3$) δ: 7.28-7.32 (m, 1H), 7.43 (d, 1H, J=3.2 Hz), 7.75-7.80 (m, 1H), 7.91 (d, 1H, J=3.2 Hz), 8.16-8.22 (m, 1H), 8.58-8.62 (m, 1H)

Example 10

Synthesis of 1-benzenesulfonyl-2-(4-methyl-2-pyridyl)indole

Tetrahydrofuran (10 ml) was charged in a nitrogen-substituted flask having an inner volume of 50 ml, cooled to −78° C., and a solution (1.6 M, 10.3 ml, 16.4 mmol) of n-butyllithium in hexane was added. To this solution was added dropwise over 10 min a solution obtained by dissolving 1-benzenesulfonylindole (4.22 g, 16.4 mmol) in tetrahydrofuran (7 ml). The reaction mixture was stirred for 30 min, and a solution obtained by dissolving 4-methyl-2-benzenesulfonylpyridine (3.00 g, 12.9 mmol) in tetrahydrofuran (5 ml) was added dropwise over 10 min. The reaction mixture was stirred for 3 hr, and isopropanol (1 ml) was added at the same temperature to stop the reaction.

The obtained reaction mixture was added to water, and the mixture was extracted with ethyl acetate (15 ml×2). The extract was concentrated and purified by silica gel chromatography to give the title compound having the following analytical data (3.25 g, yield 71% based on 4-methyl-2-benzenesulfonylpyridine) as a pale-yellow solid.

$^1$H-NMR spectrum (CDCl$_3$) δ: 2.47 (s, 3H), 6.85 (s, 1H), 7.17 (d, 1H, J=5.0 Hz), 7.19-7.33 (m, 5H), 7.47 (d, 1H, J=7.4 Hz), 7.56 (s, 1H), 7.64-7.68 (m, 2H), 8.18 (d, 1H, J=8.0 Hz), 8.60 (d, 1H, J=5.2 Hz)

INDUSTRIAL APPLICABILITY

According to the present invention, the 2-substituted pyridine derivatives (III) and (III') can be produced conveniently with fine selectivity.

This application is based on application No. 2002-214097 filed in Japan, the contents of which are incorporated hereinto by reference.

The invention claimed is:

1. A production method of a pyridine compound having a substituent at the 2-position of an aromatic heterocyclic structure, which is represented by the formula (III')

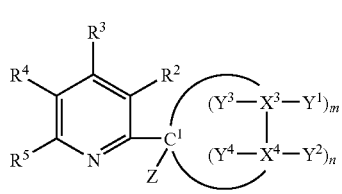

(III')

wherein R$^2$, R$^3$, R$^4$ and R$^5$ are each a hydrogen atom, a halogen atom, an alkyl group optionally having substituent(s), an aryl group optionally having substituent(s), an alkoxyl group optionally having substituent(s), an aryloxy group optionally having substituent(s), an acyloxy group optionally having substituent(s), an alkylthio group optionally having substituent(s), an arylthio group optionally having substituent(s), an arylthio group optionally having substituent(s), a protected amino group optionally having substituent(s), a nitro group, a cyano group, an acyl group optionally having substituent(s), an alkoxycarbonyl group optionally having substituent(s), a carbamoyl group optionally having substituent(s) or a sulfonyl group optionally having substituent(s), or R$^2$ and R$^3$, R$^3$ and R$^4$, or R$^4$ and R$^5$ optionally form, together with a carbon atom bonded thereto, a ring optionally having substituent(s),

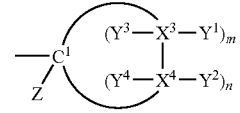

is an aromatic heterocycle optionally having substituent(s), wherein the aromatic heterocycle is selected from the group consisting of a pyridine ring, pyrimidine ring, a pyridazine ring, a pyrazine ring, a thiophene ring, a furan ring, a pyrrole ring, an imidazole ring, a pyrazole ring, a thiazole ring, an oxazole ring and an isoxazole ring; and the substituent(s) are selected from the group consisting of a halogen atom, an alkyl group optionally having substituent(s), an aryl group optionally having substituent(s), an alkoxyl group optionally having substituent(s), an aryloxy group optionally having substituent(s), an acyloxy group optionally having substituent(s), an alkylthio group optionally having substituent(s), an arylthio group optionally having substituent(s), an acylthio group optionally having substituent(s), a protected amino group optionally having substituent(s), a nitro group, a cyano group, an acyl group optionally having substituent(s), an alkoxycarbonyl group optionally having substituent(s), a carbamoyl group optionally having substituent(s) and a sulfonyl group optionally having substituent(s), which comprises reacting a 2-sulfonylpyridine compound represented by the formula (I)

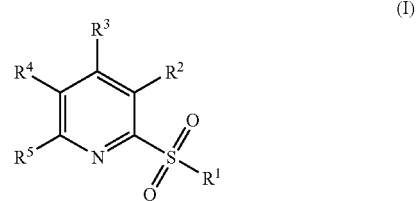

(I)

wherein
R$^1$ is an alkyl group optionally having substituent(s) or an aryl group optionally having substituent(s), and R$^2$, R$^3$, R$^4$ and R$^5$ are as defined above, with an organometallic compound represented by the formula (II')

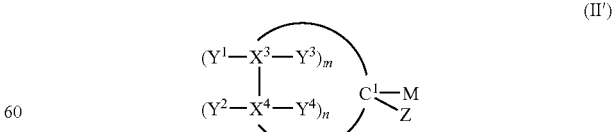

(II')

wherein
M is an atom of an element belonging to Group 1, Group 2, Group 12 or Group 13 of the periodic table except a hydrogen atom, and

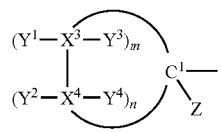

is as defined above.

2. The production method of claim 1, wherein $Y^1$ is bonded to $Y^2$, which $X^4$ adjacent to $X^3$ bonded to $Y^1$ has, to form a double bond, and at least one of $Y^3$ bonded to said $X^3$ and $Y^4$ bonded to said $X^4$ is an alkyl group optionally having substituent(s).

3. A production method of a pyridine compound having a substituent having a heterocyclic structure at the 2-position, which is represented by the formula (III)

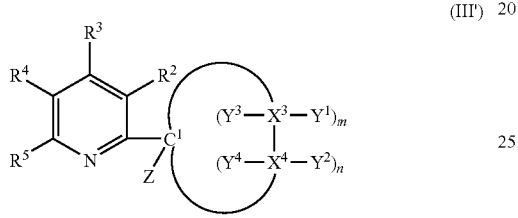

(III')

wherein
$R^2$, $R^3$, $R^4$ and $R^5$
are each a hydrogen atom, a halogen atom, an alkyl group optionally having substituent(s), an aryl group optionally having substituent(s), an alkoxyl group optionally having substituent(s), an aryloxy group optionally having substituent(s), an acyloxy group optionally having substituent(s), an alkylthio group optionally having substituent(s), an arylthio group optionally having substituent(s), an acylthio group optionally having substituent(s), a protected amino group optionally having substituent(s), a nitro group, a cyano group, an acyl group optionally having substituent(s), an alkoxycarbonyl group optionally having substituent(s), a carbamoyl group optionally having substituent(s) or a sulfonyl group optionally having substituent(s), or
$R^2$ and $R^3$, and $R^4$, or $R^4$ and $R^5$
optionally form, together with a carbon atom bonded thereto, a ring optionally having substituent(s),
m and n
are each an integer of not less than 1, wherein m+n=3 to 8,
$C^1$ is a carbon atom,
Z is a hydrogen atom, an alkyl group optionally having substituent(s) or an aryl group optionally having substituent(s),
$X^1$ is a carbon atom, CH, an oxygen atom, a nitrogen atom or a sulfur atom, and
$X^2$ is a carbon atom, CH, an oxygen atom, a nitrogen atom or a sulfur atom,
wherein at least one of $X^1$ and $X^2$ is an oxygen atom, a nitrogen atom or a sulfur atom, when $X^1$ or $X^2$ is a carbon atom, CH or a nitrogen atom, $Y^1$ and $Y^2$ are each a hydrogen atom, a halogen atom, an alkyl group optionally having substituent(s), an aryl group optionally having substituent(s), an alkoxyl group optionally having substituent(s), an aryloxy group optionally having substituent(s), an acyloxy group optionally having substituent(s), an alkylthio group optionally having substituent(s), an arylthio group optionally having substituent(s), an acylthio group optionally having substituent(s), a protected amino group optionally having substituent(s), a nitro group, a cyano group, an acyl group optionally having substituent(s), an alkoxycarbonyl group optionally having substituent(s), a carbamoyl group optionally having substituent(s) or a sulfonyl group optionally having substituent(s), and
$Y^1$, $Y^2$ or Z
is optionally bonded to or $Y^2$, which $X^1$ or $X^2$ adjacent to $X^1$, $X^2$ or $C^1$ bonded to $Y^1$, $Y^2$ or Z has, to form a double bond or a ring structure, or when $X^1$ or $X^2$ is a carbon atom, $Y^1$, or $Y^2$ shows an oxygen atom and is optionally bonded to $X^1$ or $X^2$ via a double bond,
which comprises reacting a 2-sulfonylpyridine compound represented by the formula (I)

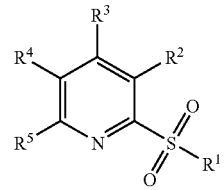

(I)

wherein
$R^1$ is an alkyl group optionally having substituent(s) or an aryl group optionally having substituent(s), and
with an organometallic compound represented by the formula (II)

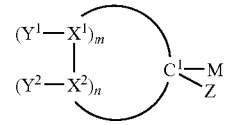

(II)

wherein
M is an atom of an element belonging to Group 1, Group 2, Group 12 or Group 13 of the periodic table except a hydrogen atom.

4. The production method of claim 3, wherein the organometallic compound (II) has an aromatic heterocycle.

5. The production method of claim 4, wherein the aromatic heterocycle is a pyridine ring, a pyrimidine ring, a pyridazine ring, a pyrazine ring, a thiophene ring, a furan ring, a pyrrole ring, an imidazole ring, a pyrazole ring, a thiazole ring, an oxazole ring or an isoxazole ring.

6. The production method of claim 3, wherein, in the formula (II), M is a lithium atom, a sodium atom, a potassium atom, a magnesium atom, a calcium atom, a zinc atom, a boron atom or an aluminum atom.

7. The production method of claim 3, wherein, in the formula (II), M is a lithium atom or a magnesium atom.

8. The production method of claim 5, wherein the aromatic heterocyclic is a pyridine ring.

9. The production method of claim 6, wherein the aromatic heterocyclic is a pyridine ring.

10. The production method of claim 7, wherein the aromatic heterocyclic is a pyridine ring.

* * * * *

UNITED STATES PATENT AND TRADEMARK OFFICE
CERTIFICATE OF CORRECTION

| | | |
|---|---|---|
| PATENT NO. | : 7,560,563 B2 | Page 1 of 1 |
| APPLICATION NO. | : 10/522195 | |
| DATED | : July 14, 2009 | |
| INVENTOR(S) | : Koyakumaru et al. | |

It is certified that error appears in the above-identified patent and that said Letters Patent is hereby corrected as shown below:

On the cover page,

Item [*] Notice:   Subject to any disclaimer, the term of this patent is extended or adjusted under 35 USC 154(b) by 517 days.

Delete the phrase "by 517 days" and insert -- by 990 days --

Signed and Sealed this

Twentieth Day of April, 2010

David J. Kappos
*Director of the United States Patent and Trademark Office*